United States Patent [19]
Courtade et al.

[11] Patent Number: 5,958,438
[45] Date of Patent: Sep. 28, 1999

[54] BORDEAUX MIXTURE, PROCESS FOR ITS MANUFACTURE AND CUPRIC FUNGICIDAL COMPOSITIONS CONTAINING IT

[75] Inventors: Michael Courtade, Le Vesinet; Georges Ramel, Rognac, both of France

[73] Assignee: Elf Atochem Agri S.A., France

[21] Appl. No.: 08/725,555

[22] Filed: Oct. 3, 1996

[30] Foreign Application Priority Data

Oct. 3, 1995 [FR] France ................................. 95 11593

[51] Int. Cl.⁶ ............................ A01N 25/04; A01N 59/20
[52] U.S. Cl. ...................... 424/405; 424/409; 424/421; 424/637
[58] Field of Search ................................. 504/100, 101; 424/405, 406, 409, 417, 421, 76.9, 637

[56] References Cited

U.S. PATENT DOCUMENTS 3,846,545  11/1974  Hess et al. ............................. 424/143

OTHER PUBLICATIONS

D.E.H. Frear: "Chemistry of Insecticides, Fungicides and Herbicides." 1948, Van Nostrand, New York XP002006216 2ième édition, chapitre XIII: copper compounds, pp. 211–217: Bordeaux mixture * p. 213, alinéa 1–alinéa 2 *.

W. Gerhartz et al.: "Ullmann's Encyclopedia of Industrial Chemistry." 1986, VCH Verlag, Weinheim, DE XP002006217 5ième édition, vol. A7, pp. 582–583: Basic Copper (II) Sulfates.

Pickering, "The Chemistry of Bordeaux Mixture," *J. Chem. Soc.* (1907) 91:1988–2001.

Martin, "Studies Upon the Copper Fungicides," *Ann. Appl. Biol.* (1932) pp. 98–120.

*Primary Examiner*—Neil S. Levy
*Attorney, Agent, or Firm*—Bell, Boyd, & Lloyd

[57] ABSTRACT

The invention relates to a Bordeaux mixture in which virtually all of the copper is in the form of brochantite and which, in dry form, contains not more than 20% by weight of bassanite.

The absence of cupric complexes other than brochantite and a small amount of bassanite in the dry product makes it possible to avoid the drawbacks of standard Bordeaux mixtures.

18 Claims, No Drawings

BORDEAUX MIXTURE, PROCESS FOR ITS MANUFACTURE AND CUPRIC FUNGICIDAL COMPOSITIONS CONTAINING IT

FIELD OF THE INVENTION

The present invention relates to the field of plant protection products and relates more particularly to a novel Bordeaux mixture, to its manufacture and to its use for the preparation of cupric fungicidal compositions in the form of powders, granules or concentrated suspensions, which are dispersible in water.

BACKGROUND OF THE INVENTION

The fungicidal treatments for vines currently in common practice find their origin in the appearance, in the 19th century, of two original fungal parasites from America:

powdery mildew (*Uncinula necator*) introduced into France in 1847 mildew (*Plasmopara viticola*) introduced into France in 1878 which have since become endemic parasites.

In order to control these parasites, use is still made of two products of inorganic origin (sulphur to combat oidium and copper to combat mildew), since their use in successive treatments does not induce any phenomenon of resistance, as is often the case with synthetic fungicides.

As regards copper, the sulphate form is seen to be the simplest to use on account of its solubility in water. However, since the acidity of this solution leads to burns on the vine leaves, it has proven necessary to incorporate a product of basic nature therein in order to decrease the acidity by neutralization. Lime and calcium carbonate have been used for this purpose, giving rise to what is known as:

Bordeaux mixture for the mixture of copper sulphate with a milk of lime,

Burgundy mixture for the mixture of copper sulphate with calcium carbonate.

Bordeaux mixture has become, little by little, the product most widely used in viticulture and its use as a fungicide has even extended to other cultures (vegetables and fruits) and to other parasites, in particular bacteriosis and scab.

The two most common processes for the industrial production of a Bordeaux mixture are:

the direct process consisting of the introduction of a milk of lime into an aqueous copper sulphate solution, the reverse process, according to which an aqueous copper sulphate solution is introduced into a milk of lime.

However, irrespective of the process used and despite the technical improvements made, the fungicidal compositions formulated from current industrial Bordeaux mixtures often have drawbacks at the time of their use, in particular:

poor dispersion in water production of a sticky deposit in the spray tank, leading to plugg nozzles appearance of burns on the leaves on account of the acidity of the product.

The use of a standard Bordeaux mixture in the formulation of a concentrated aqueous suspension (liquid formulation of the SC type) leads, on storage, to the gelation and setting and caking of the suspension to a solid. In the formulation of water-dispersible granules (formulation of WG type), the use of a standard Bordeaux mixture leads, on storage, to a reinforcement of the cohesion of the granules with, as an effect, poor redispersion of these granules during use. The use of a standard Bordeaux mixture in the formulation of a wettable powder (formulation of WP type) leads, on suspending this powder in water, to the formation of a sticky deposit.

X-ray analysis of a standard Bordeaux mixture reveals a polyphasic and variable composition of copper complexes, consisting of:

devillite: $Ca[Cu_4(SO_4)_2(OH)_6].3H_2O$ posnjakite: $Cu_4(SO_4)(OH)_6.H_2O$ brochantite: $Cu_4(SO_4)(OH)_6$ antlerite: $Cu_3(SO_4)(OH)_4$ as well as a polyphasic and variable composition of calcium complexes, consisting of:

gypsum: $CaSO_4.2H_2O$ bassanite: $CaSO_4.½H_2O$.

DESCRIPTION OF THE INVENTION

It has now been found that the abovementioned drawbacks are essentially due to the presence of cupric complexes other than brochantite and to an excess of bassanite, and that these may be remedied using a Bordeaux mixture in which virtually all of the copper is in the form of brochantite and which, in the dry form, contains not more than 20% by weight of bassanite.

The subject of the invention is thus, firstly, a Bordeaux mixture in the form of an aqueous suspension whose solids essentially consist approximately of 47% by weight of brochantite and 53% by weight of gypsum, as well as a dry Bordeaux mixture consisting approximately of 47% by weight of brochantite, from 33 to 53% by weight of gypsum and from 0 to 20% by weight of bassanite.

The subject of the invention is also a process for the manufacture of such a Bordeaux mixture of constant quality, and its use for the preparation of formulated products in commercial demand:

Bordeaux mixture as sole fungicide combination of this Bordeaux mixture with at least one synthetic fungicide in the following presentations:

formulations of WP type (wettable powder) which are dispersible in water formulations of WG type (dispersible granule) of higher apparent particle size (from about 50 to 400 μm) which are dispersible in water and release little or no dust at the time of use liquid formulations of SC type (suspension concentrate) which are also dispersible in water.

A wet Bordeaux mixture according to the invention may be obtained by reacting an aqueous copper sulphate solution and an aqueous suspension of lime at a temperature and for a period of time which are sufficient to convert virtually all of the copper complexes into brochantite.

In order to obtain the exclusive formation of brochantite, it is necessary for the $Ca(OH)_2/CuSO_4$ molar ratio to be between 0.60 and 0.75 and, preferably, between 0.65 and 0.70 approximately.

The copper concentration of the aqueous copper sulphate solution is not an essential parameter and is limited only by the solubility of the copper sulphate at the implementation temperature. Industrially, an aqueous copper sulphate solution having a copper content ranging from 20 to 100 g/l may be used. However, in order to avoid too large a dilution of the reaction medium, it is preferable to use a copper sulphate solution whose copper content is between 50 and 100 g/l and, more particularly, between 75 and 85 g/l.

The calcium hydroxide concentration of the aqueous suspension of lime is not an essential parameter either, and may vary within a wide range as a function of the particle size of the lime used. Industrially, an aqueous suspension having a $Ca(OH)_2$ content ranging from 20 to 200 g/l and, preferably, of between 100 and 150 g/l may be used.

Although the process according to the invention may be performed by simultaneously mixing the milk of lime and the aqueous copper sulphate solution or by introducing the milk of lime into the aqueous copper sulphate solution (direct process), it is preferred to work according to the reverse process consisting in introducing the aqueous copper sulphate solution into the milk of lime.

The reaction may be performed at a temperature ranging from room temperature to 90° C., but is preferably performed approximately between 40 and 70° C. The reaction time which is sufficient to convert all the copper complexes into brochantite depends on many factors, in particular on the temperature, the stirring and the concentration of the reaction medium. Under certain conditions, virtually complete conversion of the copper complexes into brochantite may be obtained in about 30 minutes. It is, however, recommended to maintain the mixture in reaction for at least two hours and, optionally, to ensure the absence of copper complexes other than brochantite by X-ray examination of the reaction product.

The reaction product is in the form of a more or less concentrated aqueous suspension which contains no bassanite and which, after possible concentration in paste form (for example by centrifugation), may be used directly for the manufacture of fungicidal formulations of SC type (suspension concentrate) or of WG type (granules) which are dispersible in water and stable on storage.

For the manufacture of wettable powders of the WP type, the paste obtained after concentration needs to be dried. In accordance with the present invention, this drying may be performed under conditions such that the bassanite content of the dry product does not exceed 20%. The content of bassanite is formed on drying depends on many factors, in particular on the temperature, the duration and the drying equipment used (oven, drying tower, drying tunnel). It may readily be controlled by analysis of the copper titre of the dry product, which should not exceed 27.3% by weight.

Starting with the Bordeaux mixture (paste or powder) according to the invention, fungicidal formulations are manufactured in a manner which is known per se, using common adjuvants (dispersing agents, wetting agents, anti-foaming agents, dyes, thickeners, inert fillers and pH modifiers). It suffices to replace the standard Bordeaux mixture (paste or powder) by a Bordeaux mixture according to the invention with an equivalent amount of copper.

EXAMPLES

In the examples which follow, which illustrate the invention without limiting it, the parts and percentages are understood to be by weight except where otherwise mentioned.

Example 1

8 liters of an aqueous suspension of lime containing 130 g/l (i.e. 14 mol of calcium hydroxide) were loaded into a reactor. Into this stirred suspension maintained at 40–50° C. were then introduced, over 5 minutes, 16 liters of an aqueous copper sulphate solution containing 80 g/l of copper (i.e. 20 mol of $CuSO_4$).

After reacting for 5 hours, the mixture was filtered and 9.66 kg of a Bordeaux mixture paste containing 50% solids (referred to hereinbelow as "BM 50 paste") were thus obtained, which paste, on drying in an oven at a temperature not exceeding 90° C., gave a solid (referred to hereinbelow as "dry BM") having the following characteristics:

copper content: 26.5%±0.5 plaster content: traces water content: <1% pH at 1% in distilled water: 6.5±0.5

X-ray analysis shows that this solid consists of a coprecipitate of brochantite (46.7%) and gypsum (53.3%), with only traces of bassanite and other copper complexes.

Example 2 (Comparative)

The process is performed as in Example 1, but with the drying being carried out at 100° C. for 10 hours. A solid, not in accordance with the invention, was thus obtained consisting of brochantite (51%) and bassanite (49%), having the following characteristics:

copper content: 28%±0.5 gypsum content: 0% water content: 0% pH at 1% in distilled water: 6.5±0.5

Example 3

75.5 parts of "dry BM", 6 parts of sodium lignosulphonate (dispersing agent), 0.5 part of sodium naphthalenesulphonate (wetting agent), 0.5 part of an anti-foaming agent (silicone) and 17.5 parts of kaolin were successively introduced into a mixer and the mixture was then ground and a wettable powder of Bordeaux mixture containing 20% of copper was obtained having, according to the CIPAC methods, the following physical characteristics:

wettability: <60 s

45 μm wet oversize: <1% suspensibility power >80% foam: <20 ml

In this water-dispersible formulation it is possible, without drawback, to add a dye such as Prussian blue.

Example 4

45.5 parts of "dry BM", 35.3 parts of technical-grade 85% mancozebe, 6 parts of sodium lignosulphonate, 0.5 part of sodium naphthalenesulphonate, 0.5 part of silicone, 1 part of Prussian blue and 11.2 parts of kaolin were loaded into the same apparatus as in Example 3.

After grinding, a wettable powder containing 12% of copper and 30% of mancozebe and having physical characteristics similar to those of the powder of Example 3 was obtained.

In this formulation, which is intended more particularly for treatment to combat vine mildew, all or part of the mancozebe may be replaced by another synthetic fungicide such as manebe, zinebe or folpel.

Example 5

56.7 parts of "dry BM", 22 parts of technical-grade 91% zinebe, 2.5 parts of technical-grade 96% cymoxanil, 6 parts of sodium lignosulphonate, 0.5 part of sodium naphthalenesulphonate, 0.5 part of silicone and 11.8 parts of kaolin were loaded into the same apparatus as in Example 3, and the mixture was then ground.

A wettable powder containing 15% of copper, 20% of zinebe and 2.4% of cymoxanil and having physical characteristics similar to those of the powder of Example 3 was thus obtained.

In this formulation more particularly intended for treatment to combat downy mildew, all or part of the zinebe may be replaced by another synthetic fungicide such as mancozebe or folpel.

Example 6

151 parts of "BM 50 paste" and 38 parts of water were mixed together in a tank fitted with a stirrer, in order to obtain a fluid paste (slurry) of low viscosity (about 100 mPa s at a shear rate of 111 s$^{-1}$) and of low particle size (2 to 5 µm).

14 parts of sodium lignosulphonate, 0.5 part of sodium naphthalenesulphonate, 0.5 part of silicone and 9.5 parts of kaolin were then introduced into this fluid paste.

The mixture was then conveyed into a drying tower (spray dryer) and granules were thus obtained which were readily dispersible in water, having the following characteristics (CIPAC method):

copper content: 20%
wettability: <30 s
45 µm wet oversize: <1%
suspensibility: >80%
foam: <20 ml

Example 7

Working as in the first paragraph of Example 6 with 129 parts of "BM 50 paste" and 32 parts of water, a fluid paste was prepared which was mixed with:

11 parts of technical-grade 91% manebe
14 parts of sodium lignosulphonate
0.5 part of sodium naphthalenesulphonate
0.5 part of silicone
9.5 parts of kaolin After drying the mixture as in Example 6, WG granules containing 17% of copper and 10% of manebe and having physical characteristics similar to those of the granules of Example 6 were obtained.

Example 8

Example 7 is repeated, but using the following constituents:

114 parts of "BM 50 paste"
28 parts of water
24 parts of technical-grade 85% mancozebe
2.5 parts of technical-grade 96% cymoxanil
14 parts of sodium lignosulphonate
0.5 part of sodium naphthalenesulphonate
0.5 part of silicone
1.5 parts of kaolin WG granules containing 15% of copper, 20% of mancozebe and 2.4% of cymoxanil, which were readily dispersible in water and had physical characteristics very close to those of the granules of Examples 6 and 7 were obtained.

Example 9

1132 g of "BM 50 paste" and 126 g of water were introduced simultaneously into a tank fitted with a stirrer, and to the fluid paste (slurry) thus obtained were then added 40 g of sodium lignosulphonate, 7.5 g of Prussian blue, 3.8 g of silicone anti-foaming agent and 90 g of an aqueous solution containing 2.5% of a thickener (polysaccharide of the xanthan gum type).

A liquid Bordeaux mixture was thus obtained containing 150 g/l of copper and having the following characteristics (CIPAC method):

45 µm wet oversize: <1%
suspensibility: >80%
foam: <20 ml

Example 10

Example 9 was repeated, but using the following constituents:

755 g of "BM 50 paste" diluted with 230 g of water
40 g of sodium lignosulphonate
5 g of sodium naphthalenesulphonate
7.5 g of Prussian blue
3.8 g of silicone anti-foaming agent
223 g of technical-grade folpel containing 90% of active material
90 g of an aqueous solution containing 2.5% of polysaccharide A stable, liquid, ready-to-use mixture containing 100 g/l of copper and 200 g/l of folpel and which had the same characteristics as the formulation of Example 9 was thus obtained.

Example 11

Example 9 was repeated, but with the following constituents:

1132 g of "BM 50 paste" diluted with 106 g of water
40 g of sodium lignosulphonate
5 g of sodium naphthalenesulphonate
7.5 g of Prussian blue
3.8 g of silicone anti-foaming agent
21 g of technical-grade cymoxanil containing 96% of active material
90 g of an aqueous solution containing 2.5% of polysaccharide A stable, liquid, ready-to-use mixture containing 150 g/l of copper and 20 g/l of cymoxanil and which had the same characteristics as the formulation of Example 9 was thus obtained.

All the formulations of Examples 3 to 11 formed the subject of tropicalization tests (storage at 54° C. for 14 days) and showed excellent stability on ageing.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. In a Bordeaux mixture, the improvement consisting of copper in the form of brochantite and not more than 20% by weight of bassanite.

2. Aqueous suspension of Bordeaux mixture according to claim 1, wherein its solids consist of about 47% by weight of brochantite and 53% by weight of gypsum.

3. Dry Bordeaux mixture according to claim 1, wherein it consists of about 47% by weight of brochantite, from 33 to 53% by weight of gypsum and from 0 to 20% by weight of bassanite.

4. Process for the manufacture of a Bordeaux mixture, comprising reacting an aqueous copper sulphate solution and an aqueous suspension of lime in a $Ca(OH)_2/CuSO_4$ molar ratio of between 0.60 and 0.75, at a temperature and for a period of time which convert the copper complexes exclusively into brochantite and not more than 20% by weight of bassanite.

5. Process according to claim 4, wherein the aqueous copper sulphate solution is added to the aqueous suspension of lime.

6. Process according to claim 4, wherein $Ca(OH)_2/CuSO_4$ molar ratio is between about 0.65 and about 0.70.

7. Process according to claim 4, wherein the reaction is performed at a temperature ranging from room temperature to 90° C.

8. Process according to claim 4, wherein the copper sulphate solution has a copper content between 50 and 100 g/l.

9. Process according to claim 4, wherein the suspension of lime has a $Ca(OH)_2$ content ranging from 20 to 200 g/l.

10. Proceeds for the manufacture of the Bordeaux mixture in which copper consists in the form of brochantite and not more than 20% by weight of bassanite, which consists of, after an optional step of concentration, drying an aqueous suspension having solids of about 47% by weight of brochantite and 53% by weight of gypsum under conditions wherein the weight content of copper in the product does not exceed 27.3%.

11. Method for making a fungicidal composition, comprising manufacturing cupric fungicidal compositions in the form of granules or concentrated suspensions, which are dispersible in water, from the Bordeaux mixture according to claim 1.

12. Method for making a fungicidal composition, comprising manufacturing cupric fungicidal compositions in the form of wettable powders, which are dispersible in water, from the Bordeaux mixture according to claim 1.

13. Cupric fungicidal compositions of a Bordeaux mixture according to claim 1.

14. Method of treatment of crops comprising fungicidally treating crops with a Bordeaux mixture to which the copper consists of brochantite and not more than 20% by weight of bassanite.

15. Process according to claim 7, wherein the temperature is between about 40 and 70° C.

16. Process according to claim 8, wherein the copper content is between 75 and 85 g/l.

17. Process according to claim 9, wherein the $Ca(OH)_2$ content is between 100 and 150 g/l.

18. A Bordeaux mixture produced by the process according to claim 4.

* * * * *